United States Patent [19]

Obata et al.

[11] Patent Number: 5,124,333

[45] Date of Patent: Jun. 23, 1992

[54] AMINOPYRIMIDINE DERIVATIVES AND HARMFUL ORGANISMS PREVENTIVE AGENT

[75] Inventors: Tokio Obata; Katsutoshi Fujii; Isamu Narita; Shoji Shikita, all of Ube, Japan

[73] Assignee: Ube Industries, Ltd., Ube, Japan

[21] Appl. No.: 558,798

[22] Filed: Jul. 26, 1990

[30] Foreign Application Priority Data

Aug. 2, 1989 [JP] Japan ................................. 1-199210
Oct. 11, 1989 [JP] Japan ................................. 1-262913

[51] Int. Cl.$^5$ ..................... A01N 43/54; C07D 239/42
[52] U.S. Cl. ..................... 514/256; 544/245; 544/278; 544/284; 544/293; 544/327
[58] Field of Search ................... 544/327; 514/256

[56] References Cited

U.S. PATENT DOCUMENTS 4,472,402  9/1984  Bononi ......................... 544/327
4,845,097  7/1989  Matsumoto et al. ........... 544/327
4,931,455  6/1991  Yoshioka et al. .............. 544/327

FOREIGN PATENT DOCUMENTS 54-17123   2/1979  Japan .
55-76803   6/1980  Japan .
55-76804   6/1980  Japan .
59-36666   2/1984  Japan .
59-36667   2/1984  Japan .
59-42387   3/1984  Japan .
61-286373  12/1986 Japan .
62-00067   1/1987  Japan .

OTHER PUBLICATIONS

Milas et al, Journal of American Chemical Society (J.A.C.S.) 80, 2189 (1958), pp. 2189–2194.

Primary Examiner—C. Warren Ivy
Assistant Examiner—James H. Turnipseed
Attorney, Agent, or Firm—Frishauf, Holtz, Goodman & Woodward

[57] ABSTRACT

An aminopyrimidine compound of the formula:

$$\text{(I)}$$

wherein
$R^1$ represents a hydrogen atom, an alkyl group, a cycloalkyl group or a halogen atom;
$R^2$ and $R^3$ each represent an alkyl group or a halogen atom, or $R^2$ and $R^3$ represent a saturated or unsaturated 5- or 6-membered ring;
$R^4$ represents a hydrogen atom or —CONR$^6$R$^7$, where $R^6$ and $R^7$ represent an unsaturated 5-membered ring; and
$R^5$ represents $$-\underset{R^8}{\text{CH}}\text{+CH}_2\text{)}_m-\overset{\text{(O)}_n}{\overset{\uparrow}{S}}-R^9 \text{ or } \text{+CH}_2\text{)}_{m'}-\overset{\text{(O)}_n}{\overset{\uparrow}{S}}-R^9,$$

where m represents an integer of 1 to 10;
m' represents an integer of 1 to 15;
n represents an integer of 0, 1 or 2;
$R^8$ represents a hydrogen atom, an alkyl group or a cycloalkyl group;
$R^9$ represents an alkyl group, an alkenyl group, an alkynyl group, a substituted or unsubstituted phenyl group, a substituted or unsubstituted aralkyl group or an alkyl group, and acid addition salts thereof. Such compound is useful for combatting insects, acarids, nematodes and fungus.

19 Claims, No Drawings

AMINOPYRIMIDINE DERIVATIVES AND HARMFUL ORGANISMS PREVENTIVE AGENT

BACKGROUND OF THE INVENTION

This invention relates to an aminopyrimidine derivative, a method for preparing the same and a harmful organisms preventive agent such as an insecticide, acaricide, nematocide and fungicide containing the same as the active ingredient.

The aminopyrimidine derivative of the present invention is a novel compound, and therefore nothing is known also about its biological activity at all.

The present inventors have investigated intensively in order to obtain a compound having excellent insecticidal, acaricidal, nematocidal and fungicidal activity to accomplish the present invention.

SUMMARY OF THE INVENTION

An object of the present invention is to provide a novel aminopyrimidine derivative, process for preparing the same and a harmful organisms preventive agent such as an insecticide, acaricide, nematocide and fungicide containing the same as the active ingredient.

The present invention provides an aminopyrimidine derivative represented by the formula:

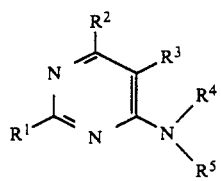

(I)

wherein
R¹ represents a hydrogen atom, an alkyl group having 1 to 4 carbon atoms, a cycloalkyl group having 3 to 6 carbon atoms or a halogen atom;
R² and R³, which may be either the same or different, each represent an alkyl group having 1 to 4 carbon atoms or a halogen atom, or R² and R³ represent a saturated or unsaturated 5- or 6-membered ring together with the carbon atom to which they are attached, said ring may be also interrupted with an oxygen atom or a sulfur atom which constitutes the ring, and also one or two alkyl group having 1 to 4 carbon atoms or halogen atom may be also substituted on said ring;
R⁴ represents a hydrogen atom or —CONR⁶R⁷, where R⁶ and R⁷ represent an unsaturated 5-membered ring together with the nitrogen atom to which they are attached and having further 1 or 2 nitrogen atom, and further an alkyl group having 1 to 4 carbon atom may be substituted or said ring; and
R⁵ represents

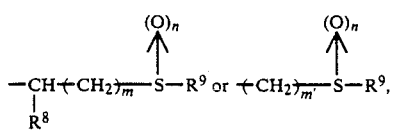

where m represents an integer of 1 to 10;
m' represents an integer of 4 to 15; n represents an integer of 0, 1 or 2

R⁸ represents a hydrogen atom, an alkyl group having 1 to 4 carbon atoms or a cycloalkyl group having 3 to 6 carbon atoms;
R⁹ represents an alkenyl group having 3 to 5 carbon atoms, an alkynyl group having 3 to 5 carbon atoms, a substituted or unsubstituted phenyl group, a substituted or unsubstituted aralkyl group, or an alkyl group having 1 to 10 carbon atoms which may be substituted by an alkoxy group having 1 to 4 carbon atoms, an alkylthio group having 1 to 4 carbon atoms, 1 to 3 halogen atom or a cycloalkyl group having 3 to 6 carbon atoms, provided that when R⁵ is

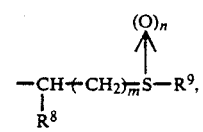

R⁴ represents a hydrogen atom and when R⁵ is

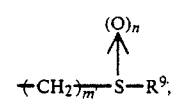

R⁴ represents —CONR⁶R⁷,
or an acid addition salt thereof, a method for preparing the same and a harmful organism preventive agent such as an insecticide, acaricide, nematocide and fungicide comprising said compound as the active ingredient.

DESCRIPTION OF THE PREFERRED EMBODIMENTS

In the above formula (I), examples of the alkyl group having 1 to 4 carbon atoms may include a methyl group, an ethyl group, a propyl group, an isopropyl group, a butyl group, an isobutyl group, a sec-butyl group and a t-butyl group.

As the alkyl group having 1 to 10 carbon atoms, there may be mentioned a methyl group, an ethyl group, a n-propyl group, a n-butyl group, a n-pentyl group, a n-hexyl group, a n-heptyl group, a n-octyl group, a n-nonyl group and a n-decyl group.

As the cycloalkyl group having 3 to 6 carbon atoms, for example, a cyclopropyl group, a cyclopentyl group and a cyclohexyl group may be mentioned.

As halogen atoms, a fluorine atom, a chlorine atom, a bromine atom and an iodine atom may be included.

As the alkenyl group having 3 to 5 carbon atoms, for example, an allyl group, a 1-butenyl group, a 2-butenyl group, a 1-methylallyl group, a 2-methylallyl group, a 2-pentenyl group and an isoprenyl group may be mentioned.

As the alkynyl group having 3 to 5 carbon atoms, for example, a 1-propynyl group, a 2-propynyl group and a 2-butynyl group may be mentioned.

As the substituted or unsubstituted phenyl group there may be included a phenyl group which may be also substituted with a lower alkyl group, a halogen atom or a halo-lower alkyl group, such as a phenyl group, a 4-chlorophenyl group, a 4-fluorophenyl group, a 4-methylphenyl group and a 4-trifluoromethylphenyl group.

As the substituted or unsubstituted aralkyl group, there may be included a benzyl group which may be also substituted with a halogen atom, a lower alkyl group or a halo-lower alkyl group, such as a benzyl group, a 4-chlorobenzyl group, a 4-fluorobenzyl group, a 4-methylbenzyl group, a 3,4-dichlorobenzyl group, an o-methylbenzyl group and an α-ethylbenzyl group.

As the alkyl group having 1 to 4 carbon atoms which may be substituted with any of an alkoxy group having 1 to 4 carbon atoms, an alkylthio group having 1 to 4 carbon atoms, a cycloalkyl group having 3 to 6 carbon atoms or 1 to 3 halogen atoms, there may be included, for example, a methoxyethyl group, an ethoxyethyl group, a proloxyethyl group, a methylthiomethyl group, a difluoromethyl group and a cyclopropylmethyl group.

Examples of the substituted or unsaturated 5- or 6-membered ring which may also contain O or S atom formed by $R^2$ and $R^3$ together with the carbon atom to which they are attached to be fused to the pyrimidine ring may include:

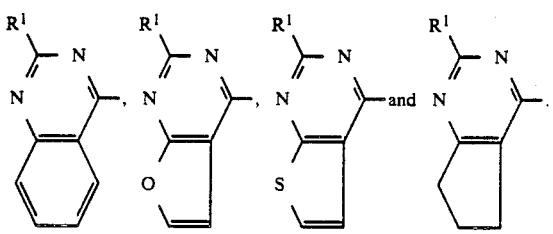

Examples of the unsaturated 5-membered ring formed by $R^6$ and $R^7$ together with the nitrogen atom to which they are attached and further containing 1 or 2 nitrogen atom may include:

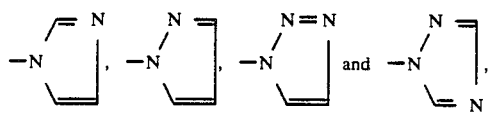

In the compound represented by the formula (I) of the present invention, the compounds represented by the following formulae (I') and (I'') are preferred.

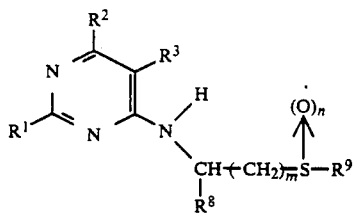

wherein $R^1$ represents a hydrogen atom, an alkyl group having 1 to 4 carbon atoms or a cycloalkyl group having 3 to 6 carbon atoms; $R^2$ and $R^3$ each represent an alkyl group having 1 to 4 carbon atom or a halogen atom, or $R^2$ and $R^3$ represent a saturated or unsaturated 5- or 6-membered ring together with the carbon atom to which they are attached, said ring may be also included one sulfur atom which constitutes the ring, and also one or two alkyl group having 1 to 4 carbon atoms or halogen atom may be also substituted on said ring; $R^8$ represents a hydrogen atom or an alkyl group having 1 to 4 carbon atoms; $R^9$ represents ;n alkenyl group having 3 to 5 carbon atoms, an alkynyl group having 3 to 5 carbon atoms, a substituted or unsubstituted phenyl group, or an alkyl group having 1 to 10 carbon atoms which may be substituted by an alkoxy group having 1 to 4 carbon atoms, an alkylthio group having 1 to 4 carbon atoms or 1 to 3 halogen atoms; m represents an integer of 1 to 10; and n represents an integer of 0, 1 or 2,

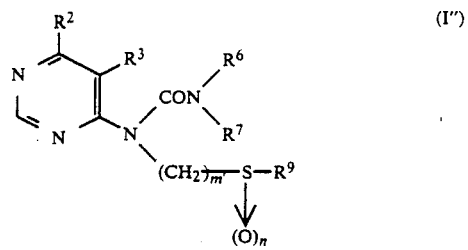

wherein $R^2$ and $R^3$, which may be either the same or different, each represent an alkyl group having 1 to 4 carbon atoms or a halogen atom, or $R^2$ and $R^3$ represent a saturated or unsaturated 5- or 6-membered ring together with the carbon atom to which they are attached, said ring may be also interrupted with an oxygen atom or a sulfur atom which constitutes the ring, and also one or two alkyl group having 1 to 4 carbon atoms or halogen.atom may be also substituted on said ring; $R^6$ and $R^7$ represent an unsaturated 5-membered ring together with the nitrogen atom to which they are attached and having further 1 or 2 nitrogen atom, and further an alkyl group having 1 to 4 carbon atom may be substituted on said ring; m' represents an integer of 4 to 15; n represents an integer of 0, 1 or 2; and $R^9$ represents an alkyl group having 1 to 4 carbon atoms, a substituted or unsubstituted phenyl group or a substituted or unsubstituted benzyl group.

In the formula (I'), preferred substituents are as follows:

$R^1$ is preferably a hydrogen atom or a straight or branched alkyl group having 1 to 4 carbon atoms, more preferably a methyl group in the alkyl group having 1 to 4 carbon atoms.

$R^2$ is preferably a straight alkyl group, more preferably a methyl group or an ethyl group.

$R^3$ is preferably a fluorine atom, a chlorine atom or a bromine atom.

$R^8$ is preferably a hydrogen atom, a methyl group, an ethyl group or a cyclopropyl group, more preferably an ethyl group.

$R^9$ is preferably a methyl group, an ethyl group, a propyl group or an isopropyl group in a lower alkyl group; an allyl group in the alkenyl group having 3 to 5 carbon atoms; a 2-propynyl group in the alkynyl group having 3 to 5 carbon atoms; a benzyl group or an α-methylbenzyl group in the aralkyl group which may have a substituent; a methoxyethyl group, an ethoxyethyl group or a propoxyethyl group in the $C_1$ to $C_4$ alkoxy-substituted alkyl group; a methylthiomethyl group in the $C_1$ to $C_4$ alkylthic-substituted $C_1$ to $C_4$ alkyl group; a difluoromethyl group in the 1 to 3 halogen-substituted $C_1$ to $C_4$ alkyl group; and a cyclopropylmethyl group.

m is preferably 1 to 10, more preferably 4 to 8.

n is preferably 0, 1 or 2.

As a ring formed by $R^2$ and $R^3$ together with the carbon atom to which they are attached to be fused to the pyrimidine ring, preferred are

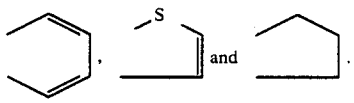

Of the compound represented by the above formula (I''), preferred are those as mentioned below.

When $R^2$ and $R^3$ are alkyl groups having 1 to 4 carbon atoms, a methyl group, an ethyl group and a propyl group are preferred, while when they are halogen atoms, a fluorine atom, a chlorine atom and a bromine atom are preferred.

It is particularly preferable that $R^2$ is a methyl group or an ethyl group, and $R^3$ is a fluorine atom, a chlorine atom or a bromine atom.

When $R^2$ and $R^3$ form a ring fused to the pyrimidine ring together with the carbon atom to which they are attached, rings of:

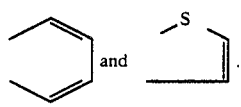

are preferred.

Examples of the unsaturated 5-membered ring formed by $R^6$ and $R^7$ together with the nitrogen atom to which they are attached may be preferably an imidazol-1-yl group, a pyrazol-1-yl group, a 1,2,3-triazol-1-yl group, a 1,2,4-triazol-1-yl group, a 2-methylimidazol-1-yl group and a 4-methylimidazol-1-yl group.

$R^9$ may be preferably a methyl group, an ethyl group, an isopropyl group and a benzyl group.

m' may be preferably 4 to 15, more preferably 6 to 8.
n may be preferably 0, 1, 2.

In the above formula (I), when either one of carbon atoms is asymmetric, individual optical isomers, racemic compounds or mixtures thereof are also included in the present invention.

As can be understood from the above formula (I), the compound of the present invention has an amino group, can form easily an acid addition salt and such salt is also included within the present invention. Examples of acid capable of forming acid addition salts may include inorganic acids such as hydrochloric acid, hydrobromic acid, nitric acid, sulfuric acid, phosphoric acid, perchloric acid; carboxylic acids such as formic acid, oxalic acid, fumaric acid, adipic acid, stearic acid, oleic acid, aconitic acid; organic sulfonic acids such as methanesulfonic acid, benzenesulfonic acid, p-toluenesulfonic acid; and sulfonamides such as saccharin.

Examples of the compounds of the formula (I) of the present invention are shown in Table 1.

TABLE 1

| Compound | $R^2$ | $R^3$ | $R^8$ | $R^9$ | m | n | Physical property |
|---|---|---|---|---|---|---|---|
| 1 | $H_5C_2$ (fused pyrimidine ring) | Cl | H | $CH_3$ | 7 | 0 | $n_D^{22.0}$ 1.5398 |
| 2 | " | " | " | $C_2H_5$ | " | " | $n_D^{23.4}$ 1.5320 |
| 3 | " | " | " | $n$-$C_3H_7$ | " | " | |
| 4 | " | " | " | $i$-$C_3H_7$ | " | " | $n_D^{23.0}$ 1.5272 |
| 5 | " | " | " | $-CH_2-C_6H_5$ | " | " | $n_D^{23.0}$ 1.5643 |
| 6 | " | " | " | $-C_6H_5$ | " | " | $n_D^{27.0}$ 1.5710 |
| 7 | " | " | " | $CH_3$ | " | 1 | m.p. 76~77° C. |
| 8 | " | " | " | " | " | 2 | m.p. 69~71° C. |
| 9 | " | " | " | $-CH_2CH=CH_2$ | " | 0 | $n_D^{23.7}$ 1.5435 |
| 10 | " | " | " | $-CH_2C\equiv CH$ | " | " | $n_D^{23.7}$ 1.5475 |

TABLE 1-continued
| | | | | | | |
|---|---|---|---|---|---|---|
| 11 | " | " | —CH$_2$CH$_2$OCH$_3$ | " | " | |
| 12 | " | " | —CH$_2$CH$_2$OC$_2$H$_5$ | " | " | n$_D^{24.2}$ 1.5274 |
| 13 | " | " |  | " | " | |
| 14 | 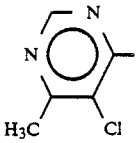 | " | CH$_3$ | " | " | n$_D^{25.5}$ 1.5416 |
| 15 | 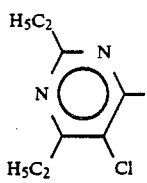 | " | " | " | " | n$_D^{26.8}$ 1.5276 |
| 16 | 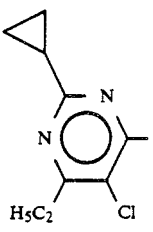 | " | " | " | " | n$_D^{26.8}$ 1.5397 |
| 17 | 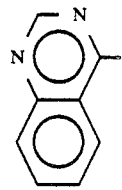 | " | " | " | " | m.p. 72~74° C. |
| 18 | 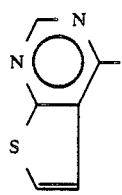 | H | CH$_3$ | 7 | 0 | m.p. 53~54° C. |
| 19 | 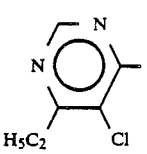 | " | " | 4 | " | |
| 20 | " | " | " | " | 5 | " | n$_D^{27.0}$ 1.5428 |
| 21 | " | " | " | " | 6 | " | n$_D^{24.8}$ 1.5397 |
| 22 | " | " | " | " | 8 | " | n$_D^{24.8}$ 1.5314 |
| 23 | " | " | CH$_3$ | " | 7 | " | |
| 24 | " | " | C$_2$H$_5$ | " | " | " | |
| 25 | " | " | i-C$_3$H$_7$ | " | " | " | |
| 26 | " | " |  | " | " | " | |
| 27 | " | " | H | " | 5 | 1 | m.p. 58~60° C. |
| 28 | " | " | " | " | " | 2 | m.p. 69~71° C. |

TABLE 1-continued

| # | Structure | | | | | Properties |
|---|---|---|---|---|---|---|
| 29 | quinoline-type (N,N bicyclic) | " | " | 7 | 1 | m.p. 120~122° C. |
| 30 | " | " | " | " | 2 | m.p. 123~125° C. |
| 31 | pyrazine with H₅C₂ and Cl | C₂H₅ | " | 6 | 0 | $n_D^{26.8}$ 1.5315 |
| 32 | pyrazine with H₃C and F | H | " | 7 | " | $n_D^{26.8}$ 1.5264 |
| 33 | pyrazine with H₅C₂ and F | " | " | " | " | NMR Data ① |
| 34 | pyrazine with H₅C₂ and CH₃ | " | " | " | " | $n_D^{24.4}$ 1.5335 |
| 35 | pyridine with H₅C₂ and C₃H₇-n | H | CH₃ | 7 | 0 | $n_D^{24.6}$ 1.5294 |
| 36 | pyrazine with H₅C₂ and Cl | " | n-C₃H₇ | 5 | " | $n_D^{24.2}$ 1.5388 |
| 37 | " | " | " | " | " | 1 | m.p. 50~53° C. |
| 38 | " | " | " | " | 2 | m.p. 92~96° C. |
| 39 | " | " | n-C₅H₁₁ | 3 | 0 | $n_D^{22.8}$ 1.5348 |
| 40 | " | " | " | " | 1 | m.p. 69~70° C. |
| 41 | " | " | " | " | 2 | m.p. 98~101° C. |
| 42 | " | " | n-C₈H₁₇ | 1 | 0 | $n_D^{23.0}$ 1.5291 |
| 43 | " | " | " | " | 1 | m.p. 98~99° C. |
| 44 | " | " | " | " | 2 | m.p. 62~65° C. |
| 45 | " | " | CH₃ | 6 | 1 | m.p. 74~76° C. |
| 46 | " | " | " | " | 2 | m.p. 68~71° C. |
| 47 | " | " | " | 8 | 1 | m.p. 75~77° C. |
| 48 | " | " | " | " | 2 | m.p. 68~70° C. |

TABLE 1-continued

| | | | | | |
|---|---|---|---|---|---|
| 49 | " | " | C₂H₅ | 7 | 1 | m.p. 47~50° C. |
| 50 | " | " | " | " | 2 | m.p. 95~98° C. |
| 51 | " | " | n-C₅H₁₁ | " | 0 | $n_D^{27.0}$ 1.5276 |
| 52 | " | " | " | " | 1 | m.p. 48~50° C. |
| 53 | (pyrazine with H₅C₂ and Cl substituents) | H | n-C₅H₁₁ | 7 | 2 | m.p. 90~92° C. |
| 54 | " | " | (phenyl) | " | 1 | $n_D^{27.2}$ 1.5666 |
| 55 | " | " | " | " | 2 | m.p. 68~70° C. |
| 56 | " | " | —CH₂SCH₃ | " | 0 | $n_D^{27.2}$ 1.5579 |
| 57 | " | " | —CH(CH₃)(phenyl) | " | 0 | $n_D^{19.4}$ 1.5602 |
| 58 | (quinoxaline) | " | n-C₃H₇ | 5 | " | m.p. 60~62° C. |
| 59 | " | " | " | " | 1 | m.p. 66~68° C. |
| 60 | " | " | " | " | 2 | m.p. 108~110° C. |
| 61 | (cyclopenta-pyrazine) | " | CH₃ | 7 | 0 | $n_D^{26.6}$ 1.5426 |
| 62 | " | " | " | " | 1 | m.p. 94~98° C. |
| 63 | " | " | " | " | 2 | m.p. 100~103° C. |
| 64 | (pyrazine with H₃C and Cl substituents) | " | " | " | 1 | m.p. 71~73° C. |
| 65 | " | " | " | " | 2 | m.p. 81~84° C. |
| 66 | (pyrazine with Cl and CH₃ substituents) | " | " | " | 0 | m.p. 65~66° C. |
| 67 | " | " | " | " | 1 | m.p. |

TABLE 1-continued
| | | | | | | |
|---|---|---|---|---|---|---|
| 68 | " | " | " | " | 2 | 91~95° C. m.p. 105~107° C. |
| 69 | 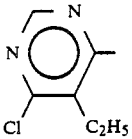 | " | " | " | 0 | $n_D^{26.6}$ 1.5457 |
| 70 | 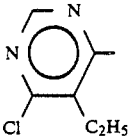 | H | $CH_3$ | 7 | 1 | m.p. 102~105° C. |
| 71 | " | " | " | " | 2 | m.p. 116~118° C. |
| 72 | 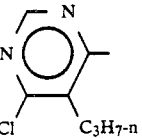 | " | " | " | 0 | m.p. 40~42° C. |
| 73 | " | " | " | " | 1 | m.p. 81~83° C. |
| 74 | " | " | " | " | 2 | m.p. 117~120° C. |
| 75 | 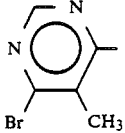 | " | " | " | 0 | $n_D^{24.6}$ 1.5422 |
| 76 | " | " | " | " | 1 | m.p. 124~127° C. |
| 77 | " | " | " | " | 2 | m.p. 102~104° C. |
| 78 | 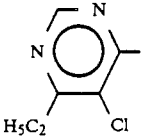 | " | " | " | 0 | m.p. 45~48° C. |
| 79 | " | " | " | " | 1 | m.p. 90~91° C. |
| 80 | " | " | " | " | 2 | m.p. 102~104° C. |
| 81 |  | " | $CHF_2$ | " | 0 | $n_D^{24.5}$ 1.5283 |
| 82 | Oxalate of {Compound 1.(COO)$_2$} Compound 1 | | | " | 0 | m.p. 105~106° C. |
| 83 | Hydrochloride {Compound 1.HCl} of Compund 1 | | | " | 0 | m.p. 75~77° C. |
(NMR Data ①)
$^1$H-NMR(CDCl$_3$, δ ppm)
1.25(3H, t), 1.25~1.50(8H, b), 1.50~1.75(4H, m),
2.00(3H, s), 2.50(2H, t), 2.70(2H, dq), 3.50(2H, q),
4.90~5.10(1H, b), 8.30(1H, d)

TABLE 1-continued
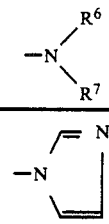
(I″)
| Compound No. | $R^2$ | $R^3$ | $-N\begin{smallmatrix}R^6\\R^7\end{smallmatrix}$ | $R^9$ | m | n | Physical property |
|---|---|---|---|---|---|---|---|
| 84 | $C_2H_5$ | Cl |  | $CH_3$ | 8 | 0 | $n_D^{22.6}$ 1.5425 |
| 85 | " | " | 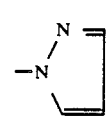 | " | " | " | $n_D^{22.6}$ 1.5432 |
| 86 | " | " | " | " | " | 2 | $n_D^{24.0}$ 1.5363 |
| 87 | " | " | 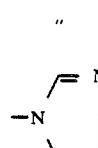 | i-$C_3H_7$ | " | 0 | $n_D^{23.1}$ 1.5374 |
| 88 | " | " | 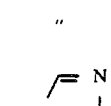 | " | " | " | $n_D^{22.0}$ 1.5370 |
| 89 | " | " | " | $C_2H_5$ | " | " | $n_D^{23.0}$ 1.5399 |
| 90 | $C_2H_5$ | Cl |  | 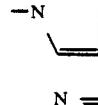 | 8 | 0 | $n_D^{23.0}$ 1.5702 |
| 91 | " | " | 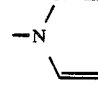 | 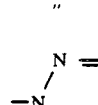 | " | " | $n_D^{23.0}$ 1.5667 |
| 92 | " | " | 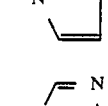 | " | " | " | $n_D^{23.0}$ 1.5657 |
| 93 | " | " |  | $CH_3$ | 6 | " | $n_D^{27.0}$ 1.5489 |
| 94 | " | " | 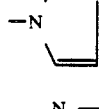 | " | " | " | $n_D^{27.0}$ 1.5474 |
| 95 | $CH_3$ | " |  | " | 8 | " | $n_D^{25.8}$ 1.5455 |

TABLE 1-continued

| | | | | |
|---|---|---|---|---|
| 96 | " " | (pyrazoline ring structure) | " | " $n_D^{25.5}$ 1.5430 |
| 97 | (dimethylphenyl) | (pyrazoline ring structure) | " | " $n_D^{25.0}$ 1.5712 |
| 98 | " | (pyrazoline ring structure) | " | " $n_D^{25.0}$ 1.5684 |

Of these compounds, preferred are as follows.
1. 5-Chloro-6-ethyl-4-(8-methylthiooctylamino)pyrimidine
2. 5-Chloro-6-ethyl-4-(8-ethylthiooctylamino)pyrimidine
4. 5-Chloro-6-ethyl-4-(8-i-propylthiooctylamino)pyrimidine
5. 5-Chloro-6-ethyl-4-(8-benzylthiooctylamino)pyrimidine
6. 5-Chloro-6-ethyl-4-(8-phenylthiooctylamino)pyrimidine
7. 5-Chloro-6-ethyl-4-(8-methylsulfoxyoctylamino)pyrimidine
8. 5-Chloro-6-ethyl-4-(8-methylsulfonyloctylamino)pyrimidine
9. 5-Chloro-6-ethyl-4-(8-allylthiooctylamino)pyrimidine
10. 5-Chloro-6-ethyl-4-(8-propargylthiooctylamino)pyrimidine
12. 5-Chloro-6-ethyl-4-[8-(2-ethoxyethylthio)octylamino]pyrimidine
14. 5-Chloro-6-methyl-4-(8-methylthiooctylamino pyrimidine
18. 4-(8-Methylthiooctylamino)thieno[2,3-d]pyrimidine
20. 5-Chloro-6-ethyl-4-(6-methylthiohexylamino)pyrimidine
21. 5-Chloro-6-ethyl-4-(7-methylthioheptylamino pyrimidine
22. 5-Chloro-6-ethyl-4-(9-methylthiononylamino)pyrimidine
31. 5-Chloro-6-ethyl-4-(7-methylthio-1-ethylheptylamino)pyrimidine
33. 6-Ethyl-5-fluoro-4-(8-methylthiooctylamiro)pyrimidine
36. 5-Chloro-6-ethyl-4-(6-n-propylthiohexylamino)pyrimidine
56. 5-Chloro-6-ethyl-4-(8-methylthiomethylthiooctylamino)pyrimidine
66. 6-Chloro-5-methyl-4-(8-methylthiooctylamino)pyrimidine
78. 5-Bromo-6-methyl-4-(8-methylthiooctylamiro)pyrimidine
81. 5-Chloro-6-ethyl-4-(8-difluoromethylthiooctylamino)pyrimidine
82. 5-Chloro-6-ethyl-4-(8-methylthiooctylamiro)pyrimidine oxalate
83. 5-Chloro-6-ethyl-4-(8-methylthiooctylamiro)pyrimidine hydrochloride
84. 5-Chloro-N-(imidazole-1-ylcarbonyl)-N-(8-methylthiooctyl)-6-ethyl-4-pyrimidineamine
85. 5-Chloro-N-(pyrazole-1-ylcarbonyl)-N-(8-methylthiooctyl)-6-ethyl-4-pyrimidineamine
87. 5-Chloro-N-(imidazole-1-ylcarbonyl)-N-(8-i-propylthiooctyl)-6-ethyl-4-pyrimidineamine
88. 5-Chloro-N-(pyrazole-1-ylcarbonyl)-N-(8-i-propylthiooctyl)-6-ethyl-4-pyrimidineamine
89. 5-Chloro-N-(pyrazole-1-ylcarbonyl)-N-(8-ethylthiooctyl)-6-ethyl-4-pyrimidineamine
91. 5-Chloro-N-(imidazole-1-ylcarbonyl)-N-(8-benzylthiooctyl)-6-ethyl-4-pyrimidineamine
93. 5-Chloro-N-(imidazole-1-ylcarbonyl)-N-(6-methylthiooctyl)-6-ethyl-4-pyrimidineamine
95. 5-Chloro-N-(imidazole-1-ylcarbonyl)-N-(8-methylthiooctyl)-6-methyl-4-pyrimidineamine
96. 5-Chloro-N-(pyrazole-1-ylcarbonyl)-N-(8-methylthiooctyl)-6-methyl-4-pyrimidineamine
98. N-(Pyrazole-1-ylcarbonyl)-N-(8-methylthiooctyl)-4quinazolineamine Among them, particularly preferred are Compounds Nos. 1, 2, 6, 10, 20, 21, 22, 31, 33, 66, 84, 85, 89, 91, 93, 95, 96 and 98.

The compound (I) of the present invention can be prepared by the process shown below.

Preparation process A

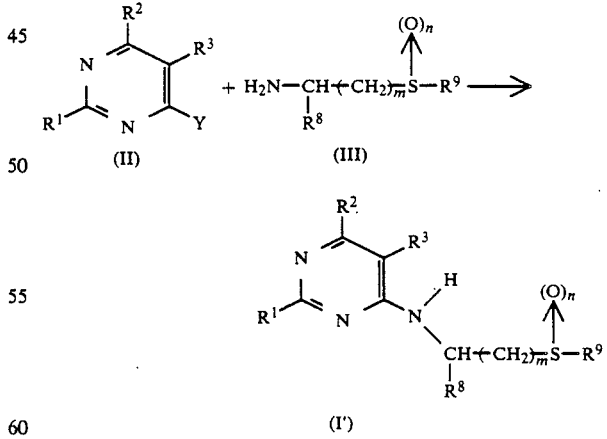

wherein $R^1$, $R^2$, $R^3$, $R^8$, $R^9$, m and n have the same meanings as defined above, and Y represents an eliminatable group.

The eliminatable group Y is not particularly limited at all, and there may be mentioned, for example, a halogen atom such as a chlorine atom, a bromine atom and an iodine atom; an alkylthio group such as a methylthio group, an ethylthio group, a propylthio group and a butylthio group; an alkanesulfonyloxy group which may be substituted by a halogen atom such as a methanesulfonyloxy group an ethanesulfonyloxy group and a trifluoromethanesulfonyoxy group; an arylsulfonyloxy group such as a benzenesulfonyloxy group and a p-toluenesulfonyloxy group; a mercapto group and a hydroxyl group.

As clearly seen from the above reaction formulae, in the present reaction, a compound H-Y is eliminated so that in order to proceed the reaction smoothly by capturing the compound, it is preferred to carry out the reaction in the presence of a base. The reaction is generally carried out in the presence of a solvent, but the compound of the formula (II) and that of the formula (III) may be reacted by heating in the absence of a solvent.

The solvent is not particularly limited, provided that it does not participate in the present reaction, as exemplified by aromatic, aliphatic alicyclic hydrocarbons which are chlorinated or not such as benzene, toluene xylene, methylnaphthalene, petroleum ether, ligroin, hexane, chlorobenzene, dichlorobenzene, methylene chloride, chloroform, dichloroethane, trichloroethylene, cyclohexane; ethers such as dimethyl ether, diethyl ether, tetrahydrofuran, dioxane; ketones such as acetone, methyl ethyl ketone; alcohols such as methanol, ethanol and ethylene glycol or a hydrate thereof; amides such as N,N-dimethylformamide (DMF) and N,N-dimethylacetamide; organic bases such as pyridine and N,N-diethylaniline; and mixtures of the above-mentioned solvents.

As the base, there may be included organic base such as triethylamine, pyridine and N,N-diethylaniline; alkali metal alkoxides such as sodium methoxide and sodium ethoxide; inorganic bases such as sodium hydride, sodium amide, sodium hydroxide, potassium hydroxide, sodium carbonate and potassium carbonate.

The reaction temperature is not particularly limited, but generally from room temperature to a boiling point of the solvent or lower, and heating the mixture is preferred in order to shorten the reaction time.

Preparation process B

In the above formula (I'), the compound (I - 1) wherein n is 0 can be also prepared by the following known process.

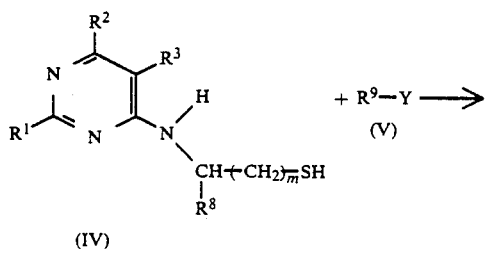

(IV)

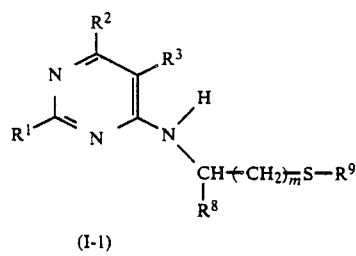

(I-1)

wherein $R^1$, $R^2$, $R^3$, $R^8$, $R^9$ and m have the same meanings as defined above, and Y represents an eliminatable group.

In the present reaction, a compound H-Y is eliminated so that in order to proceed the reaction smoothly by capturing the compound, it is preferred to carry out the reaction in the presence of a base. The reaction is generally carried out in the presence of a solvent, but the compound of the formula (IV) and that of the formula (V) may be reacted by heating in the absence of a solvent.

As the solvent and the base, they are not particularly limited so long as they do not participate the present reaction, and, for example, the solvent and the base used in the above mentioned preparation process A can be used.

The reaction temperature is not particularly limited, but generally from room temperature to a boiling point of the solvent or lower, and heating the mixture is preferred in order to shorten the reaction time.

Preparation process C

In the above formula (I'), the compound (I - 2) wherein n is 1 or 2 can be also prepared by the following known process.

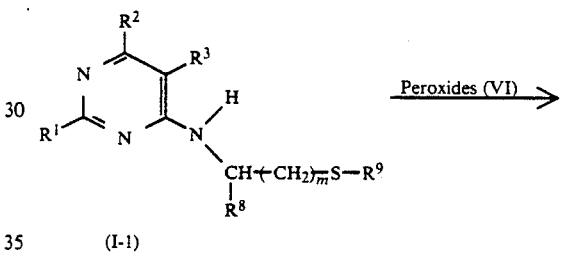

(I-1)

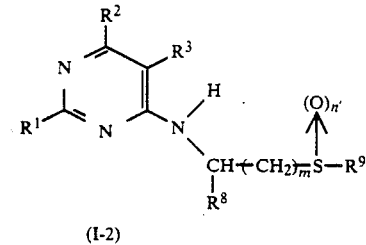

(I-2)

wherein $R^1$, $R^2$, $R^3$, $R^8$, $R^9$ and m have the same meanings as defined above, and n' is 1 or 2.

The peroxides (VI) are not particularly limited, and there may be mentioned, for example, hydrogen peroxide, m-chloroperbenzoic manganate and sodium hypochlorite.

As the solvent, it is not particularly limited so long as it do not participate the present reaction, and there may be mentioned, for example, chlorinated aliphatic hydrocarbons such as chloroform and dichloromethane; alcohols such as methanol and ethanol; ketones such as acetone and methyl ethyl ketone; cyclic ethers such as tetrahydrofuran and dioxane; aliphatic carboxylic acids such as acetic acid and propionic acid; water and mixtures of the above solvents.

The reaction temperature is not particularly limited, but the reaction can be carried out at $-10°$ C. to a boiling point of the solvent or lower, but preferably $-10°$ C. to room temperature.

The starting compound of the formula (III) can be prepared by, for example, the following process which has been known itself.

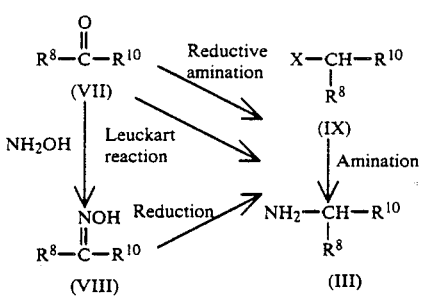

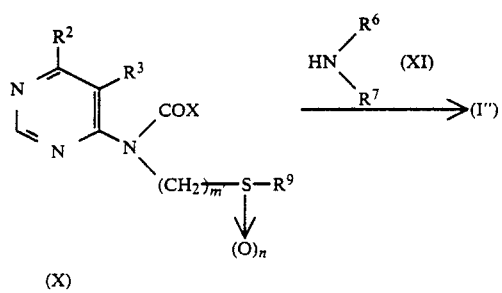

wherein $R^{10}$ represents a group $-(CH_2)_m-S-R^9$; $R^8$, $R^9$, m and n have the same meanings as defined above and X represents a halogen atom.

Preparation process D wherein $R^1$ to $R^3$, $R^6$, $R^7$, $R^9$, m' and n have the same meaning as defined above; and X represents a halogen atom.

As is apparent from the above reaction scheme, since an acid is eliminated in the present reaction, and for carrying out smoothly the reaction by capturing this, it is preferred to carry out the reaction in the presence of a base.

The reaction is generally carried out in the presence of a solvent. The solvent is not particularly limited, provided that it does not participate in the present invention, as exemplified by aromatic, aliphatic alicyclic hydrocarbons which are chlorinated or not such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, ethylene glycol dimethyl ether, tetrahydrofuran and dioxane; ketones such as acetone and methyl ethyl ketone; amides such as N,N-dimethylformamide and N,N-dimethylacetamide; and mixtures of the above-mentioned solvents.

As the base, there may be included organic bases such as triethylamine, pyridine and N,N-diethylaniline; alkali metal alkoxides such as sodium methoxide and sodium ethoxide; inorganic bases such as sodium hydride, sodium amide, sodium hydroxide, potassium hydroxide, sodium carbonate and potassium carbonate, but preferred bases are organic bases such as triethylamine and pyridine.

Further, in order to accelerate the reaction rate, it is preferred to add a catalytic amount of a 4-N,N-substituted-aminopyridine such as 4-N,N-dimethylaminopyridine and 4-pyrrolidinopyridine.

The reaction temperature is not particularly limited, but generally 0° C. or higher and not higher than the solvent employed, but it is preferred to carry out the reaction at 5° C. to room temperature.

In the above preparation method, the compound of the formula (X) used as the starting material can be prepared easily by the method know per se as shown below.

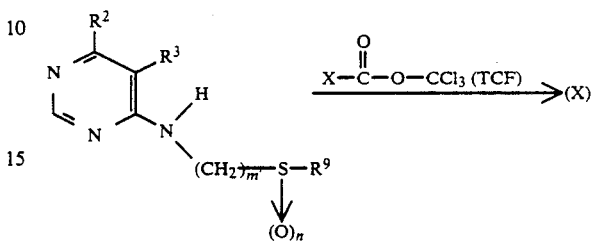

wherein $R^2$, $R^3$, $R^6$, $R^9$, m', n and X have the same meaning as defined above; and TCF is an abbreviation of trichloromethylhalogen formate.

In the present invention, hydrochloric acid is eliminated, and therefore for carrying out smoothly the reaction by capturing this, it is preferred to carry out the reaction in the presence of a base.

The reaction is carried out generally in the presence of a solvent, and the solvent is not particularly limited, provided that it does not participate in the present reaction, and the solvents to be used for the reaction between the compound of the formula (X) and that of the formula (XI) as mentioned above can be employed.

Examples of the base may include organic bases such as triethylamine, pyridine and N,N-dimthylaniline, but preferably organic bases such as triethylamine and pyridine.

The reaction temperature is not particularly limited, but generally 0° C. or higher and not higher than the boiling point of the solvent employed, but it is preferred to carry out the reaction at 5° C. or lower.

The compound (X) obtained by the present reaction can be also used for the reaction with the compound of the following formula (XI) without isolation and purification.

In the present preparation process, the compound of the formula (XII) to be used as the starting material can be prepared easily according to the method as described below.

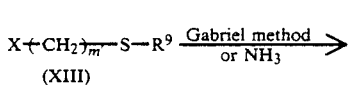

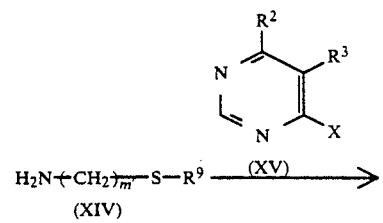

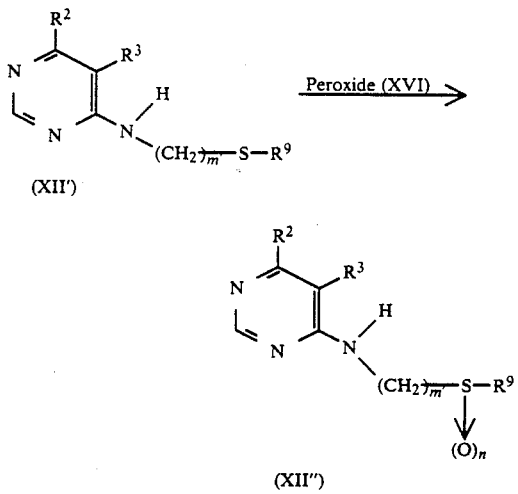

wherein $R^2$, $R^3$, $R^9$, m', n and X are the same as defined above.

The peroxide (XVI) is not particularly limited, but, for example, hydrogen peroxide, m-chloroperbenzoic acid, sodium metaperiodate, potassium permanganate and sodium hypochlorite may be included.

The desired product (I) obtained by the above-described method can be purified conveniently by known means such as recrystallization and various chromatographics.

The acid addition salt can be obtained easily by dissolving the compound of the formula (I) in an appropriate solvent, as exemplified by aromatic, aliphatic, alicyclic hydrocarbons which are chlorinated or not, such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, ethylene glycol dimethyl ether, tetrahydrofuran and dioxane; and ketones such as acetone and methyl ethyl ketone, and introducing an acid during the reaction, or alternatively introducing an acid into the reaction after completion of the reaction.

The compounds (I) of the present invention exhibit excellent effects against agricultural and horticultural injurious insects, including Hemiptera such as planthoppers, leafhoppers, aphids and whiteflies; Lepidoptera such as pyralid cabbage army worms, diamondback moth, leaf roller worms, pyralid moths and common cabbage worms; Coleoptera such as weevils and leaf beetles; and otherwise Acarina such as citrus red mite and twospotted spider mite. Also, they are effective for control of hygienically injurious insects such as flies, mosquitoes and cockroaches, and otherwise also effective against injurious insects to stored grains.

Further, the compounds (I) of the present invention are also extremely effective against root-knot nematodes, pine wood nematode and bulb mites. Particularly, against rootknot nematodes, they exhibit excellent effects by both the solid treatment and the stalk and leaf treatment. Therefore, the insecticide of the present invention is used in broad a sense, including insecticide, acaricide and nematocide in a narrow sense.

Also, the compounds (I) of the present invention are effective for injurious diseases for agriculture and horticulture, and have activities against, for example, rice blast, barley powdery mildew, and otherwise wheat red rust, cucumber gray mold, cucumber downy mildew and tomato epidemic.

Thus, the compounds of the present invention have extremely wide uses and applications, having high activities, and can be provided for practical application in various preparation forms.

The insecticide, acaricide, nematocide and fungicide of the present invention comprise one or several kinds of the compounds of the formula (I) as the active ingredient. Although the compound (I) itself may be used, it is generally used by formulating conventional carriers surfactants, dispersing agents or auxiliary agents which are acceptable in the field, in a conventional manner to be prepared into such compositions as powder, wettable powder, emulsion, fine granule, granule, aqueous or oily suspension and aerosol before use.

Suitable carriers may include solid carriers such as talc, bentonite, clay, kaolin, diatomaceous earth, white carbon, vermicullite, slaked lime, siliceous sand, ammonium sulfate and urea; liquid carriers such as hydrocarbons such as kerosene and mineral oil; aromatic hydrocarbons such as benzene, toluene and xylene; chlorinated hydrocarbons such as chloroform and carbon tetrachloride; ethers such as dioxane and tetrahydrofuran; ketones such as acetone, cyclohexanone and isophorone; esters such as ethyl acetate, ethylene glycol acetate and dibutyl maleate; alcohols such as methanol, n-hexanol and ethylene glycol; polar solvents such as dimethylformamide and dimethyl sulfoxide; or water. As the gaseous carrier, by use of air, nitrogen, carbon dioxide and Freon, the compound can be mixed and jetted.

Also, as the surfactants, dispersing agents for effecting improvements of performances of the present agent such as attachment onto animals and plants, improvement of absorption, dispersion, emulsification and spreading of the medicament, there may be employed, for example, alcohol sulfuric acid esters, alkylsulfonic acid salts, ligninsulfonic acid salts and polyoxyethylene glycol ethers.

Further, for amelioration of the properties of the preparation, as auxiliary agents, for example, carboxymethyl cellulose, polyethylene glycol and gum arabic may be employed.

The above-mentioned carrier, surfactant, dispersing agent and auxiliary agent may be employed individually or in a combination depending on the respective purposes.

The active ingredient concentration when the compound (I) of the present invention is formed into a preparation may be generally 1 to 50% by weight for emulsion, generally 0.3 to 25% by weight for powder, generally 1 to 90% by weight for wettable agent, generally 0.5 to 5% by weight for granule, generally 0.5 to 5% by weight for oil agent, and generally 0.1 to 5% by weight for aerosol.

These preparations can be diluted to appropriate concentrations and provided for various uses depending on the respective purposes by spraying onto stalks and leaves of plants, soil and water surface of paddy field, or by direct application.

The present invention is described in more detail by referring to Examples, but these Examples are not limitative of the scope of the present invention at all.

Reference Example

Synthesis of 5-chloro-N-chlorocarbonyl-N-(8-methylthiooctyl)-6-ethyl-4-pyrimidineamine Into a solution of 2.0 g of trichloromethylchloroformate (TCF) dissolved in 20 ml of toluene and cooled to 5° C. or lower was added dropwise under stirring a solution of 3.2 g of 5-chloro-N-(8-methylthiooctyl)-6-ethyl-4-pyrimidineamine and 4.0 g of triethylamine dissolved in 20 ml of toluene. After the dropwise addition, the mixture was stirred at room temperature for 5 hours. After completion of the reaction, 20 ml of water was added, and the mixture was stirred at room temperature for 30 minutes to decompose excessive TCF.

The toluene layer was separated, washed with water, dried over anhydrous sodium sulfate, followed by evaporation of the solvent under reduced pressure, to give 3.2 g of the desired product which is a pale yellow oily liquid.

In the same manner as mentioned above, 5-chloro-N-(6-methylthiohexyl)-6-ethyl-4-pyrimidineamine, 5-chloro-N-chlorocarbonyl-N-(8-methylthiooctyl)-6-methyl-4-pyrimidineamine and N-chlorocarbonyl-N-(8-methylthiooctyl-4-quinazolineamine were synthesized.

EXAMPLE 1

Synthesis of 5-chloro-6-ethyl-4-(8-methylthiooctylamino)pyrimidine (Compound No. 1)

The title compound (I) can be obtained according to the preparation process A as mentioned below.

In 50 ml of toluene were dissolved 4.0 g of 8-methylthiooctylamine and 4 ml of triethylamine, and 4.0 g of 4,5-dichloropyrimidine was added to the solution and the mixture was refluxed for 5 hours under stirring.

After completion of the reaction, formed triethylamine hydrochloride was removed by filtration, and the filtrate was condensed under reduced pressure.

The resulting oily product was isolated by a column chromatography Wako Gel C-200, trade name, eluted with toluene:ethyl acetate=3:1) to obtain 5.7 g of the desired product as colorless oily liquid.

EXAMPLE 2

Synthesis of 5-chloro-6-ethyl-4-8-(1-phenylethylthio)octylamino]-pyrimidine (Compound No. 57)

The title compound (I) can be obtained according to the preparation process B as mentioned below.

To 10 ml of dimethylformamide (DMF) were added 0.80 g of 5-chloro-6-ethyl-4-(8-mercaptooctylamino) pyrimidine which is the starting compound (IV), 0.58 g of 1-phenylethyl bromide and 0.55 g of potassium carbonate and the mixture was heated under stirring at 100° C. for 5 hours.

After completion of the reaction, the reaction mixture was extracted by using ethyl acetate, and the extract was washed with water, dried over anhydrous sodium sulfate and ethyl acetate was removed by evaporation under reduced pressure.

The resulting oily product was isolated by a silica gel column chromatography (Wako Gel C-200, trade name, eluted with toluene:ethyl acetate=3 : 1) to obtain 0.85 g of the desired product as colorless oily product.

EXAMPLE 3

Synthesis of 5-chloro-6-ethyl-4-(8-methylsulfinyloctylamino)pyrimidine (Compound No. 7)

The title compound (I) can be obtained according to the preparation process C as mentioned below.

In 8 ml of water was dissolved 0.8 g of sodium metaperiodate and after cooling to 0° C. under stirring a solution of 1.2 g of the compound of Compound No. 1 obtained in Example 1 which is the starting compound (I - 1) dissolved in 5 ml of ethanol was added dropwise.

After completion of the dropwise addition, the mixture was stirred at the same temperature for one hour to complete the reaction. Ethanol was removed by evaporation from the reaction mixture under reduced pressure and the residue was extracted with ethyl acetate. The extract was washed with water, dried over anhydrous sodium sulfate, and then ethyl acetate was removed by evaporation under reduced pressure.

The resulting oily product was isolated by a column chromatography (Wake Gel C-200, trade name, eluted with ethyl acetate : ethanol=9:1) to obtain 0.8 g of the desired product as colorless powder.

EXAMPLE 4

Synthesis of 5-chloro-6-ethyl-4-(8-methylsulfonyloctylamino)-pyrimidine (Compound No. 8)

The title compound (I) can be obtained according to the preparation process C as mentioned below.

In 30 ml of dichloromethane was dissolved 2.0 g of Compound No. 1 which is the starting compound (I - 1) obtained in Example 1 and the solution was cooled to 5° C. or lower, and 3.0 g of m-chloroperbenzoic acid was added under stirring and the mixture was stirred for further 3 hours. After completion of the reaction, the reaction mixture was washed with an 1 N aqueous sodium hydroxide solution and then with water, dried over anhydrous sodium sulfate, and dichloromethane was removed by evaporation under reduced pressure.

The resulting oily product was isolated by a silica gel column chromatography (Wako gel C-200, trade name, eluted with toluene:ethyl acetate=1 : 1) to obtain 1.8 g of the desired product as colorless powdery crystals.

EXAMPLE 5

Synthesis of Compounds No. 2 to No. 6 and No. 9 to No. 56. No. 58 to No 81 in Table 1

In the same manner as in any of Examples 1 to 4, the title compound (I) (shown as Compounds No. 2 to No. 6, No. 9 to No. 56, No. 58 to No. 81 in Table 1) can be obtained.

EXAMPLE 6

Synthesis of 5-chloro-N-imidazol-1-ylcarbonyl)-N-(8-methylthiooctyl)-6-ethyl-4-pyrimidineamine (Compound No. 84)

The title compound (I) can be obtained according to the preparation process D as mentioned below.

Into a solution of 0.1 g of imidazole and 0.2 g of triethylamine dissolved in 10 ml of toluene was added under stirring a solution of 0.4 g of 5-chloroN-chlorocarbonyl-N-(8-methylthiooctyl)-6-ethyl-4-pyrimidineamine dissolved in 10 ml of toluene, and the mixture was stirred at room temperature for one hour.

After completion of the reaction, the triethylamine hydrochloride formed was separated by filtration, and washed with a small amount of toluene. The filtrate and the washing were combined, and the solvent was removed by evaporation. The resultant pale yellow oily product was isolated by column chromatography (Wako Gel C-200, trade name, eluted with toluene:ethyl acetate=3:1) to give 0.4 g of the desired product as a colorless oily liquid.

EXAMPLE 7

Synthesis of N-(8-methylthiooctyl)-N-(pyrazole-1-ylcarbonyl)-4-quinazolineamine (Compound No. 98)

The title compound (I) can be obtained according to the preparation process D as mentioned below.

Into a solution of 0.1 g of pyrazole and 0.2 g of triethylamine dissolved in 10 ml of toluene was added dropwise under stirring a solution of 0.4 g of N-chlorocarbonyl-N-(8-methylthiooctyl)-4-quinazolineamine dissolved in 5 ml of toluene, and further a catalytic amount of 4-N,N-dimethylaminopyridine (DMAP) was added, followed by stirring at room temperature for one hour. After completion of the reaction, the triethylamine hydrochloride formed was separated by filtration and washed with a small amount of toluene. The filtrate and the washing were combined, and the solvent was evaporated under reduced pressure. The resultant pale yellow oily product was isolated by column chromatography (Wako Gel C-200, trade name, eluted with toluene:ethyl acetate=9:1) to give 0.4 g of the desired product which is a pale yellow oily liquid.

EXAMPLE 8

5 Parts by weight of the compound of Compound No. 1, 35 parts by weight of bentonite, 57 parts by weight of talc, 1 part by weight of Neopelex powder (trade name; manufactured by Kao Atlas) and 2 parts by weight of sodium ligninsulfonate were uniformly mixed, and then kneaded with addition of a small amount of water, followed by granulation and drying, to give granules.

EXAMPLE 9

10 Parts by weight of the compound of Compound No. 1, 70 parts of kaolin, 18 parts by weight of white carbon, 1.5 parts by weight of Neopelex powder (trade name: manufactured by Kao Atlas) and 0.5 part by weight of Demol (trade name; manufactured by Kao Atlas) were uniformly mixed, and the pulverized to give a wettable agent.

EXAMPLE 10

To 20 parts by weight of the compound of Compound No. 7 and 70 parts by weight of xylene were added 10 parts by weight of Toxanone (trade name: manufactured by Sanyo Kasei Kogyo), followed by uniform mixing and dissolution, to give an emulsion.

EXAMPLE 11

5 Parts by weight of the compound of Compound No. 84, 50 parts by weight of talc and 45 parts by weight of kaolin were uniformly mixed to give a powder.

EXAMPLE 12

Activity test against diamondback moth

The compounds shown in Table 1 were formulated similarly as described in Example 8, and each formulation was diluted with water containing a surfactant (0.01%) to 100 ppm to prepare a chemical solution. In each chemical solution, cabbage leaf strip (5 cm×5 cm) was dipped for 30 seconds, and placed in a plastic cup. After air drying, ten 3rd-instar diamondback moth larvae were freed, and &he plastic cup was closed with a lid and left to stand in a thermostatic chamber of 25° C. Two days later, the numbers of live and dead insects were counted to determine the % mortality. The results are shown in Table 2.

In Table 2, those with mortality of 100% are shown as A, those with 99 to 80% as B, those with 79 to 60% as C, and those with 59% or less as D.

TABLE 2

| Compound No. | Activity against diamondback moth |
|---|---|
| 1 | A |
| 2 | B |
| 4 | A |
| 5 | B |
| 7 | A |
| 8 | B |
| 14 | A |
| 17 | B |
| 18 | B |
| 20 | B |
| 21 | B |
| 22 | A |
| 29 | B |
| 31 | A |
| 33 | A |
| 34 | A |
| 36 | A |
| 45 | B |
| 47 | A |
| 48 | B |
| 56 | A |
| 57 | B |
| 67 | B |
| 75 | B |
| 77 | B |
| 81 | A |
| 82 | A |
| 83 | A |

EXAMPLE 13

Activity test against diamondback moth

The compounds shown in Table 1 were formulated similarly as described in Example 8, and each formulation was diluted with water containing a surfactant (0.01%) to 1000 ppm to prepare a chemical solution. In each chemical solution, a cabbage leaf strip (5 cm×5 cm) was dipped for 30 seconds, and placed in a plastic cup. After air drying, ten 3rd-instar diamondback moth larvae were freed, and the plastic cup was closed with a lid and left to stand in a thermostatic chamber of 25° C. Two days later, the numbers of live and dead insects were counted to determine the % mortality. The results are shown in Table 3.

In Table 3, those with mortality of 100% are shown as A, those with 99 to 80% as B, those with 79 to 60% as C, and those with 59% or less as D.

TABLE 3

| Compound No. | Activity against diamondback moth |
|---|---|
| 84 | A |
| 85 | A |
| 86 | A |
| 87 | A |
| 88 | A |
| 89 | A |

TABLE 3-continued

| Compound No. | Activity against diamondback moth |
| --- | --- |
| 93 | A |
| 94 | A |
| 95 | B |
| 96 | B |
| 97 | B |
| 98 | B |

EXAMPLE 14

Activity test against brown rice planthopper

The compounds shown in Table 1 were formulated similarly as described in Example 8, and each formulation was diluted with water containing a surfactant (0.01%) to 300 ppm to prepare a chemical solution. In each chemical solution dipped were young rice seedlings for 30 seconds, and the rice seedlings after air drying were inserted into a glass cylinder. Ten 3rd instar brown rice planthopper nymph were freed into the cylinder, and the cylinder was left to stand stoppered with a porous plug in a thermostatic chamber of 25° C. Four days later, the numbers of live and dead insects were counted to determine the % mortality. The results are shown in Table 4.

In Table 4, those with mortality of 100% are shown as A, those with 99 to 80% as B, those with 79 to 60% as C, and those with 59% or less as D.

TABLE 4

| Compound No. | Activity against brown rice planthopper |
| --- | --- |
| 1 | B |
| 2 | B |
| 4 | B |
| 7 | A |
| 8 | A |
| 12 | B |
| 18 | B |
| 20 | B |
| 21 | B |
| 22 | A |
| 27 | A |
| 28 | B |
| 31 | A |
| 36 | A |
| 47 | B |
| 48 | B |
| 49 | B |
| 56 | A |
| 75 | A |
| 76 | B |
| 81 | A |
| 82 | A |
| 83 | A |

EXAMPLE 15

Activity test against green rice leafhopper

The compounds shown in Table 1 were formulated similarly as described in Example 8, and each formulation was diluted with water containing a surfactant (0.01%) to 1000 ppm to prepare a chemical solution. In each chemical solution were dipped young rice seedlings for 30 seconds, and the rice seedlings after air drying were inserted into a glass cylinder. Ten 4th instar green rice leafhopper nymph were freed into the cylinder, and the cylinder was left to stand stoppered with a porous plug in a thermostatic chamber of 25° C. Four days later, the numbers of live and dead insects were counted to determine the % mortality. The results are shown in Table 5.

In Table 5, those with mortality of 100% are shown as A, those with 99 to 80% as B, those with 79 to 60% as C, and those with 59% or less as D.

TABLE 5

| Compound No. | Activity against green rice leafhopper |
| --- | --- |
| 84 | A |
| 85 | A |
| 86 | A |
| 87 | A |
| 88 | A |
| 89 | A |
| 93 | B |
| 96 | B |
| 98 | A |

EXAMPLE 16

Activity test against female adult two-spotted spider mite

10 Female adult two-spotted spider mites were provided for the test together with kidney bean leaf strips (diameter 20 mm). On the other hand, the compounds shown in Table 1 were formulated similarly as described in Example 8, and each formulation was diluted to 300 ppm with water containing a surfactant (0.01%) to prepare a chemical solution, and leaf strips were dipped in each solution for 10 seconds. The leaf strips were left to stand in a thermostatic chamber of 25° C. Three days later, the numbers of live and dead mites were counted to determine the % mortality.

In Table 6, those with mortality of 100% are shown as A, those with 99 to 80% as B, those with 79 to 60% as C, and those with 59% or less as D.

TABLE 6

| Compound No. | Activity against female adult two-spotted spider mite |
| --- | --- |
| 1 | A |
| 2 | A |
| 4 | A |
| 6 | A |
| 9 | A |
| 10 | A |
| 12 | A |
| 14 | A |
| 20 | A |
| 21 | A |
| 22 | A |
| 31 | A |
| 32 | A |
| 33 | A |
| 34 | B |
| 36 | A |
| 42 | A |
| 47 | A |
| 57 | A |
| 75 | A |
| 81 | A |
| 82 | A |
| 83 | A |

EXAMPLE 17

Activity test against male adult two-spotted spider mite

10 Female adult two-spotted spider mites were provided for the test together with mulberry leaf strips (diameter 20 mm). On the other hand, the compounds shown in Table 1 were formulated similarly as described in Example 8, and each formulation was diluted to 1000 ppm with water containing a surfactant (0.01%) to prepare a chemical solution, and leaf strips were dipped in each solution for 10 seconds. The leaf strips were left to stand in a thermostatic chamber of 25° C. Three days later, the numbers of live and dead mites were counted to determine the % mortality.

In Table 7, those with mortality of 100% are shown as A, those with 99 to 80% as B, those with 79 to 60% as C, and those with 59% or less as D.

TABLE 7

| Compound No. | Activity against female adult two-spotted spider mite |
|---|---|
| 84 | A |
| 85 | A |
| 87 | A |
| 88 | A |
| 89 | A |
| 90 | B |
| 91 | B |
| 92 | B |
| 93 | B |
| 94 | A |
| 96 | B |
| 98 | B |

EXAMPLE 18

Activity test against sweet potato root-knot nematode

The compounds shown in Table 1 were formulated similarly as described in Example 8, and each formulation wa: diluted with water to 20 ppm to prepare a chemical solution. 0.5 ml of the solution was sampled into a test tube, and further 0.5 ml of a liquid containing 30 to 40 sweet potato root-knot nematodes was added. The mixture was left to stand in a thermostatic chamber of 25° C., and two days later, the numbers of live and dead nematodes were counted under microscope to determine the % mortality of the nematodes. The results are shown in Table 8.

In Table 8, those with mortality of 100% are shown as A, those with 99 to 80% as B, those with 79 to 60% as C, and those with 59% or less as D.

TABLE 8

| Compound No. | Activity against sweet potato root-knot nematode |
|---|---|
| 1 | A |
| 2 | A |
| 4 | A |
| 5 | A |
| 6 | A |
| 7 | A |
| 8 | A |
| 9 | A |
| 10 | A |
| 12 | A |
| 14 | A |
| 17 | A |
| 18 | A |
| 20 | A |
| 21 | A |
| 22 | A |
| 27 | A |
| 28 | A |
| 29 | A |
| 30 | A |
| 31 | A |
| 32 | A |
| 33 | A |
| 34 | A |
| 36 | A |
| 37 | A |
| 38 | B |

TABLE 8-continued

| Compound No. | Activity against sweet potato root-knot nematode |
|---|---|
| 39 | A |
| 42 | A |
| 45 | A |
| 46 | A |
| 47 | A |
| 48 | A |
| 49 | A |
| 50 | A |
| 51 | A |
| 52 | A |
| 54 | A |
| 56 | A |
| 57 | A |
| 58 | A |
| 59 | A |
| 60 | B |
| 61 | A |
| 62 | A |
| 63 | B |
| 64 | A |
| 65 | A |
| 66 | A |
| 67 | A |
| 68 | A |
| 69 | A |
| 70 | A |
| 71 | A |
| 75 | A |
| 76 | A |
| 77 | B |
| 78 | A |
| 79 | B |
| 80 | A |
| 81 | A |
| 82 | A |
| 83 | A |
| 84 | A |
| 85 | A |
| 87 | A |
| 88 | A |
| 89 | A |
| 91 | A |
| 93 | A |
| 94 | A |
| 95 | A |
| 96 | A |
| 97 | B |
| 98 | B |

EXAMPLE 19

Control activity test against barley powdery mildew (preventive effect)

Ten barleys (species: Kuromugi) were grown per pot of a plastic planting pot of 6 cm in diameter, and a wettable agent prepared as described in Example 8 diluted to 500 ppm with water containing a surfactant (0.01%) was sprayed onto the young plant at the 1.5 leaf stage in an amount of 20 ml per pot.

After spraying, the plants were harvested in a glass greenhouse for 2 days, and then the barley powdery mildew conidia were collected from the afflicted leaves and inoculated by spraying uniformly on the plants.

After inoculation, the plants were grown in a glass greenhouse for one week, and the extent of the barley powdery mildew lesion appearing in the first leaf was examined. The chemical agent effect was judged by comparison with the extent of the lesion of the non-treated district.

Evaluation is shown by the 6 ranks of 5 to 0, and those without lesion evaluated as 5, those with lesion area of 10% or less as compared with the non-treated district as 4, those of about 20% as 3, those of about 40% as 2, those of about 60% as 1, and those wholly afflicted as 0. The results are shown in Table 9.

TABLE 9

| Compound No. | Effect |
| --- | --- |
| 84 | 4 |
| 85 | 5 |
| 88 | 5 |
| 89 | 5 |
| 90 | 5 |
| 91 | 5 |
| 92 | 5 |
| 96 | 5 |
| Non-treated | 0 |

EXAMPLE 20

Control activity test against wheat rust (preventive effect)

Ten wheats (species: Kobushikomugi) were grown per pot of a plastic planting pot of 6 cm in diameter, and a wettable agent prepared as described in Example 8 diluted to 500 ppm with water containing a surfactant (0.01%) was sprayed onto the young plant at the 1.5 leaf stage in an amount of 20 ml per pot.

After spraying, the plants were harvested in a glass greenhouse for 2 days, and then the wheat red rust spore suspension ($7 \times 10^4$ spores/ml) was inoculated by spraying uniformly on the plants.

After inoculation, the plants were grown in a glass greenhouse for one week, and the extent of the wheat read rust lesion appearing in the first leaf was examined. The chemical agent effect was judged by comparison with the extent of the lesion of the non-treated district. Evaluation is shown by the 6 ranks of 5 to 0, and those without lesion evaluated as 5, those with lesion area of 10 % or less as compared with the non-treated district as 4, those of about 20% as 3, those of about 40% as 2, those of about 60% as 1, and those wholly afflicted as 0. The results are shown in Table 10.

TABLE 10

| Compound No. | Effect |
| --- | --- |
| 1 | 5 |
| 2 | 5 |
| 4 | 5 |
| 5 | 5 |
| 6 | 5 |
| 7 | 5 |
| 8 | 5 |
| 9 | 5 |
| 10 | 5 |
| 14 | 5 |
| 17 | 4 |
| 18 | 4 |
| 20 | 4 |
| 21 | 5 |
| 22 | 5 |
| 27 | 4 |
| 28 | 5 |
| 31 | 5 |
| 32 | 4 |
| 34 | 5 |
| 36 | 5 |
| 37 | 4 |
| 38 | 5 |
| 39 | 4 |
| 40 | 5 |
| 41 | 5 |
| 42 | 4 |
| 43 | 4 |
| 44 | 5 |
| 45 | 5 |
| 46 | 5 |

TABLE 10-continued

| Compound No. | Effect |
| --- | --- |
| 47 | 5 |
| 48 | 5 |
| 49 | 4 |
| 50 | 5 |
| 51 | 5 |
| 52 | 5 |
| 53 | 4 |
| 54 | 5 |
| 60 | 4 |
| 64 | 5 |
| 69 | 5 |
| 70 | 4 |
| 81 | 5 |
| 82 | 5 |
| 83 | 5 |
| 84 | 5 |
| 85 | 5 |
| 87 | 5 |
| 88 | 5 |
| 89 | 5 |
| 90 | 5 |
| 91 | 5 |
| 92 | 5 |
| 93 | 5 |
| 94 | 5 |
| 95 | 5 |
| 96 | 5 |
| 97 | 4 |
| 98 | 5 |
| Non-treated | 0 |

EXAMPLE 21

Control activity test against rice blast (preventive effect)

Ten rices (species: Nipponbare) were grown per pot of a plastic planting pot of 6 cm in diameter, and a wettable agent prepared as described in Example 8 diluted to 500 ppm with water containing a surfactant (0.01%) was sprayed onto the young plant at the 1.5 leaf stage in an amount of 20 ml per pot.

After spraying, the plants were harvested in a glass greenhouse for 2 days, and then the rice blast conidia were prepared from the afflicted leaves and inoculated by spraying uniformly on the plant leaves.

After inoculation, the plants were grown in a greenhouse at 28° C. for 5 days, and the extent of the rice blast lesion appearing in the leaf was examined. The chemical agent effect was judged by comparison with the extent of the lesion of the non-treated district.

Evaluation is shown by the 6 ranks of 5 to 0, and those without lesion evaluated as 5, those with lesion area of 10% or less as compared with the non-treated district as 4, those of about 20% as 3, those of about 40% as 2, those of about 60% as 1, and those wholly afflicted as 0. The results are shown in Table 11.

TABLE 11

| Compound No. | Effect |
| --- | --- |
| 1 | 5 |
| 4 | 5 |
| 5 | 4 |
| 7 | 4 |
| 9 | 5 |
| 10 | 5 |
| 14 | 5 |
| 15 | 4 |
| 20 | 4 |
| 21 | 4 |
| 27 | 5 |
| 28 | 5 |
| 30 | 4 |

TABLE 11-continued

| Compound No. | Effect |
| --- | --- |
| 32 | 5 |
| 37 | 4 |
| 38 | 4 |
| 39 | 5 |
| 41 | 4 |
| 42 | 4 |
| 44 | 4 |
| 45 | 4 |
| 46 | 5 |
| 47 | 5 |
| 48 | 4 |
| 61 | 4 |
| 62 | 5 |
| 69 | 4 |
| 70 | 4 |
| 81 | 5 |
| 82 | 4 |
| 83 | 4 |
| 87 | 5 |
| 88 | 5 |
| 89 | 5 |
| 90 | 5 |
| 91 | 4 |
| 92 | 5 |
| 93 | 5 |
| 94 | 5 |
| 95 | 5 |
| 96 | 5 |
| 97 | 4 |
| 98 | 5 |
| Non-treated | 0 |

As seen from the above results, the compound of the formula (I) and its acid addition salt of the present invention is useful as an agricultural chemical having excellent insecticidal, acaricidal, nematocidal and fungicidal activities.

We claim:

1. An aminopyrimidine compound represented by the formula:

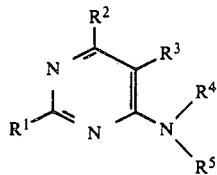 (I)

wherein $R^1$ represents a hydrogen atom, an alkyl group having 1 to 4 carbon atoms, a cycloalkyl group having 3 to 6 carbon atoms or a halogen atom;

$R^2$ and $R^3$, which may be either the same or different, each represent an alkyl group having 1 to 4 carbon atoms or a halogen atom;

$R^4$ represents a hydrogen atom; and $R^5$ represents

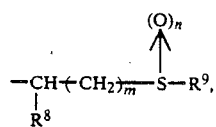

where m represents an integer of 1 to 10;
n represents an integer of 0, 1 or 2;
$R^8$ represents a hydrogen atom, an alkyl group having 1 to 4 carbon atoms or a cycloalkyl group having 3 to 6 carbon atoms;

$R^9$ represents an alkenyl group having 3 to 5 carbon atoms, an alkynyl group having 3 to 5 carbon atoms, a substituted or unsubstituted phenyl group, a substituted or unsubstituted aralkyl group, or an alkyl group having 1 to 10 carbon atoms which is unsubstituted or substituted by an alkoxy group having 1 to 4 carbon atoms, an alkylthio group having 1 to 3 carbon atoms, 1 to 3 halogen atoms or a cycloalkyl group having 3 to 6 carbon atoms, or an acid addition salt thereof.

2. The aminopyrimidine compound according to claim 1, wherein $R^1$ is an alkyl group having 1 to 4 carbon atoms.

3. The aminopyrimidine compound according to claim 1, wherein $R^9$ is said alkyl group having 1 to 10 carbon atoms and is a methyl group, an ethyl group, a n-propyl group, a n-butyl group, a n-pentyl group, a n-hexyl group, a n-heptyl group, a n-octyl group, a n-nonyl group or a n-decyl group.

4. The aminopyrimidine compound according to claim 1, wherein $R^1$ is a halogen atom.

5. The aminopyrimidine compound according to claim 1, wherein $R^9$ is said alkenyl group having 3 to 5 carbon atoms and is an allyl group, a 1- or 2-butenyl group, a 1- or 2-methylallyl group, a 2-pentenyl group or an isoprenyl group.

6. The aminopyrimidine compound according to claim 1, wherein $R^9$ is said alkynyl group having 3 to 5 carbon atoms and is a 1- or 2-propynyl group or a 2-butynyl group.

7. The aminopyrimidine compound according to claim 1, wherein $R^9$ is said substituted or unsubstituted phenyl group and is a phenyl group, a 4-chlorophenyl group, a 4-fluorophenyl group, a 4-methylphenyl group or a 4-trifluoromethylphenyl group.

8. The aminopyrimidine compound according to claim 1, wherein $R^9$ is said substituted or unsubstituted aralkyl group and is a benzyl group, a 4-chlorobenzyl group, a 4-fluorobenzyl group, a 4-methylbenzyl group, a 3,4-dichlorobenzyl group, an α-methylbenzyl group or an α-ethylbenzyl group.

9. The aminopyrimidine compound according to claim 1, wherein $R^9$ is said alkyl group having 1 to 10 carbon atoms which is unsubstituted or substituted with an alkoxy group having 1 to 4 carbon atoms, an alkylthio group having 1 to 4 carbon atoms, 1 to 3 halogen atoms or a cycloalkyl group having 3 to 6 carbon atoms and wherein $R^9$ is a methoxyethyl group, an ethoxyethyl group, a propoxyethyl group, a methylthiomethyl group, a difluoromethyl group or a cyclopropylmethyl group.

10. The aminopyrimidine compound according to claim 1, wherein said compound is represented by the formula:

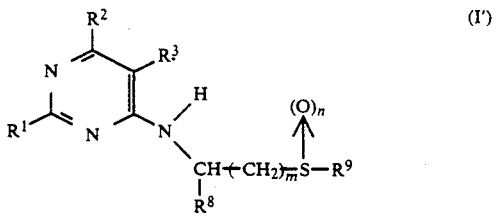 (I')

wherein $R^1$ represents a hydrogen atom, an alkyl group having 1 to 4 carbon atoms or a cycloalkyl group having 3 to 6 carbon atoms;

$R^2$ and $R^3$ each represent an alkyl group having 1 to 4 carbon atoms or a halogen atom, $R^8$ represents a hydrogen atom or an alkyl group having 1 to 4 carbon atoms;

$R^9$ represents an alkenyl group having 3 to 5 carbon atoms, an alkynyl group having 3 to 5 carbon atoms, a substituted or unsubstituted phenyl group, or an alkyl group having 1 to 10 carbon atoms which is unsubstituted or substituted by an alkoxy group having 1 to 4 carbon atoms, an alkylthio group having 1 to 4 carbon atoms or 1 to 3 halogen atoms;

m represents an integer of 1 to 10; and n represents an integer of 0, 1 or 2.

11. The aminopyrimidine derivative according to claim 10, wherein $R^1$ is a hydrogen atom, $R^2$ is a methyl group or an ethyl group, $R^3$ is a fluorine atom, a chlorine atom or a bromine atom, $R^8$ is a hydrogen atom, a methyl group, an ethyl group or a cyclopropyl group, $R^9$ is a lower alkyl group selected from the group consisting of a methyl group, an ethyl group, a propyl group and an isopropyl group, a lower alkoxyethyl group selected from the group consisting of a methoxyethyl group, an ethoxyethyl group and an i-propoxyethyl group, a methylthiomethyl group or a difluoromethyl group, m is 4 to 8, n is 0, 1 or 2.

12. The aminopyrimidine compound according to claim 10, wherein said compound is selected from the group consisting of:
5-chloro-6-ethyl-4-(8-methylthiooctylamino)pyrimidine,
5-chloro-6-ethyl-4-(8-ethylthiooctylamino)pyrimidine,
5-chloro-6-ethyl-4-(8-i-propylthiooctylamino)pyrimidine,
5-chloro-6-ethyl-4-(8-benzylthiooctylamino)pyrimidine,
5-chloro-6-ethyl-4-(8-phenylthiooctylamino)pyrimidine,
5-chloro-6-ethyl-4-(8-methylsulfoxyoctylamino)pyrimidine,
5-chloro-6-ethyl-4-(8-methylsulfonyloctylamino)pyrimidine,
5-chloro-6-ethyl-4-(8-allylthiooctylamino)pyrimidine,
5-chloro-6-ethyl-4-(8-propargylthiooctylamino)pyrimidine,
5-chloro-6-ethyl-4-[8-(2-ethoxyethylthio)octylamino]pyrimidine,
5-chloro-6-ethyl-4-(8-methylthiooctylamino)pyrimidine,
5-chloro-6-ethyl-4-(6-methylthiohexylamino)pyrimidine,
5-chloro-6-ethyl-4-(7-methylthioheptylamino)pyrimidine,
5-chloro-6-ethyl-4-(9-methylthiononylamino)pyrimidine,
5-chloro-6-ethyl-4-(7-methylthio-1-ethylheptylamino)pyrimidine,
6-ethyl-5-fluoro-4-(8-methylthiooctylamino)pyrimidine,
5-chloro-6-ethyl-4-(6-n-propylthiohexylamino)pyrimidine,
5-chloro-6-ethyl-4-(8-methylthiomethylthiooctylamino)pyrimidine,
6-chloro-6-ethyl-4-(8-methylthiooctylamino)pyrimidine,
5-bromo-6-methyl-4-(8-methylthiooctylamino)pyrimidine,
5-chloro-6-ethyl-4-(8-difluoromethylthiooctylamino)pyrimidine,
5-chloro-6-ethyl-4-(8-methylthiooctylamino)pyrimidine oxalate and
5-chloro-6-ethyl-4-(8-methylthiooctylamino)pyrimidine hydrochloride.

13. The aminopyrimidine compound according to claim 12, wherein the compound is selected from the group consisting of
5-chloro-6-ethyl-4-(8-methylthiooctylamino)pyrimidine,
5-chloro-6-ethyl-4-(8-ethylthiooctylamino)pyrimidine,
5-chloro-6-ethyl-4-(8-methylthiooctylamino)pyrimidine,
6-ethyl-5-fluoro-4-(8-methylthiooctylamino)pyrimidine, and
5-chloro-6-ethyl-4-(8-difluoromethylthiooctylamino)pyrimidine.

14. The aminopyrimidine compound according to claim 13, wherein the compound is selected from the group consisting of
5-chloro-6-ethyl-4-(8-methylthiooctylamino)pyrimidine,
5-chloro-6-ethyl-4-(8-methylthiooctylamino)pyrimidine, and
6-ethyl-5-fluoro-4-(8-methylthiooctylamino)pyrimidine.

15. An insecticidal, acaricidal, nematocidal and fungicidal composition comprising a carrier and an insecticidal, acaricidal, nematocidal or fungicidal effective amount of the aminopyrimidine compound of the formula (I) defined in claim 1 or an acid addition salt thereof.

16. A method for combatting insects, acarids, nematodes and fungus comprising applying thereto or to a locus thereof an insecticidal, acaricidal, nematocidal or fungicidal effective amount of the compound of formula (I) defined in claim 1 or an acid addition salt thereof.

17. The method according to claim 16, wherein the compound is selected from the group consisting of
5-chloro-6-ethyl-4-(8-methylthiooctylamino)pyrimidine,
5-chloro-6-ethyl-4-(8-ethylthiooctylamino)pyrimidine,
5-chloro-6-ethyl-4-(8-i-propylthiooctylamino)pyrimidine,
5-chloro-6-ethyl-4-(8-benzylthiooctylamino)pyrimidine,
5-chloro-6-ethyl-4-(8-phenylthiooctylamino)pyrimidine,
5-chloro-6-ethyl-4-(8-methylsulfoxyoctylamino)pyrimidine,
5-chloro-6-ethyl-4-(8-methylsulfonyloctylamino)pyrimidine,
5-chloro-6-ethyl-4-(8-allylthiooctylamino)pyrimidine,
5-chloro-6-ethyl-4-(8-propargylthiooctylamino)pyrimidine,
5-chloro-6-ethyl-4-[8-(2-ethoxyethylthio)octylamino]pyrimidine,
5-chloro-6-ethyl-4-(8-methylthiooctylamino)pyrimidine,
4-(8-methylthiooctylamino)thieno[2,3-d]pyrimidine,
5-chloro-6-ethyl-4-(6-methylthiohexylamino)pyrimidine,
5-chloro-6-ethyl-4-(7-methylthioheptylamino)pyrimidine, 5-chloro-6-ethyl-4-(9-methylthiononylamino)pyrimidine,
5-chloro-6-ethyl-4-(7-methylthio-1-ethylheptylamino)pyrimidine,
6-ethyl-5-fluoro-4-(8-methylthiooctylamino)pyrimidine,
5-chloro-6-ethyl-4-(6-n-propylthiohexylamino)pyrimidine,
5-chloro-6-ethyl-4-(8-methylthiomethylthiooctylamino)pyrimidine,
6-chloro-5-methyl-4-(8-methylthiooctylamino)pyrimidine,
5-bromo-6-methyl-4-(8-methylthiooctylamino)pyrimidine,
5-chloro-6-ethyl-4-(8-difluoromethylthiooctylamino)pyrimidine,
5-chloro-6-ethyl-4-(8-methylthiooctylamino)pyrimidine oxalate and
5-chloro-6-ethyl-4-(8-methylthiooctylamino)pyrimidine hydrochloride.

18. The method according to claim 17, wherein the compound is selected from the group consisting of
5-chloro-6-ethyl-4-(8-methylthiooctylamino)pyrimidine,
5-chloro-6-ethyl-4-(8-ethylthiooctylamino)pyrimidine,
5-chloro-6-ethyl-4-(8-methylthiooctylamino)pyrimidine,
6-ethyl-5-fluoro-4-(8-methylthiooctylamino)pyrimidine, and
5-chloro-6-ethyl-4-(8-difluoromethylthiooctylamino)pyrimidine.

19. The method according to claim 18, wherein the compound is selected from the group consisting of
5-chloro-6-ethyl-4-(8-methylthiooctylamino)pyrimidine,
5-chloro-6-ethyl-4-(8-methylthiooctylamino)pyrimidine, and
6-ethyl-5-fluoro-4-(8-methylthiooctylamino)pyrimidine.

* * * * *